United States Patent [19]

Cleary

[11] Patent Number: 4,934,932
[45] Date of Patent: Jun. 19, 1990

[54] DISPENSER FOR ORTHODONTIC O-RINGS

[75] Inventor: James D. Cleary, Glendora, Calif.

[73] Assignee: Unitek Corporation, Monrovia, Calif.

[21] Appl. No.: 282,453

[22] Filed: Dec. 8, 1988

[51] Int. Cl.⁵ ............................................. A61C 7/00
[52] U.S. Cl. ........................................ 433/18; 433/11
[58] Field of Search ............... 221/25, 26, 69, 87, 221/302; 206/63.3, 63.5, 330, 343, 345, 346, 805; 29/413; 433/11, 15, 17, 18, 19

[56] References Cited

U.S. PATENT DOCUMENTS

| | | | |
|---|---|---|---|
| 3,193,094 | 7/1965 | Schulstad | 206/43.5 |
| 3,361,251 | 7/1966 | Olsson | 206/330 |
| 3,530,583 | 9/1970 | Klein et al. | 32/14 |
| 3,903,601 | 9/1975 | Anderson et al. | 32/14 D |
| 4,038,753 | 8/1977 | Klein | 32/14 E |
| 4,217,686 | 8/1980 | Dragan | 29/413 |
| 4,667,845 | 5/1987 | Frazier et al. | 222/25 X |

FOREIGN PATENT DOCUMENTS 1247695 10/1960 France ............................. 206/343

Primary Examiner—Kevin P. Shaver
Assistant Examiner—W. T. Waffner
Attorney, Agent, or Firm—Donald M. Sell; Walter N. Kirn; James D. Christoff

[57] ABSTRACT

A unitary dispenser for elastomeric orthodontic devices such as ligatures and teeth separators has a circular carrier band that carries a series of the devices. A central, flat web is connected to the inner periphery of the band and extends across the middle of the dispenser to provide a centrally disposed gripping section. The web is preferably thinner than the carrier band and thus facilitates one-handed manipulation of the dispenser without visual observation. In use, the dispenser is rotated about a central axis when the web is gripped between a thumb and forefinger in order to bring each of the O-rings into a convenient position for detachment from the carrier band.

6 Claims, 1 Drawing Sheet

4,934,932

DISPENSER FOR ORTHODONTIC O-RINGS

BACKGROUND OF THE INVENTION

1. Field of the Invention

This invention relates to a hand-held dispenser for elastomeric, ring-shaped orthodontic devices.

2. Description of the Related Art

Ring-shaped elastomeric devices for orthodontic treatment are available in a variety of configurations and are useful for applications such as separating adjacent teeth, ligating archwire to brackets, or shifting teeth toward desired respective positions in proper alignment with adjacent teeth. Devices of this type are sometimes loosely packaged in bulk form, or instead are molded together in the form of a chain. In other instances, a series of elastomeric devices are integrally molded with a larger carrier portion that functions as a disposable dispenser.

One type of unitary, commercially available elastomeric dispenser has an open center, ring-shaped carrier band with a series of elastic ligatures molded both around the inner periphery as well as the outer periphery of the band. Another type of known dispenser is described in U.S. Pat. No. 4,038,753 and includes a central, open center ring-shaped section along with two elongated, opposed, outwardly extending branches that each carry along their length a plurality of O-ring ligatures.

It has been found, however, that satisfactory manipulation of orthodontic elastomeric dispensers is a highly personalized matter and depends upon the preferences of the orthodontist. As an example, it is somewhat difficult for some individuals to rotate circular dispensers having an open center in order to bring each of the molded devices into a convenient position for separation from the dispenser.

SUMMARY OF THE INVENTION

The present invention is directed toward an orthodontic O-ring dispenser which has a ring-shaped carrier band, and a series of elastomeric, orthodontic O-rings are integrally, detachably connected to the periphery of the carrier band. The O-rings are spaced apart from each other and extend in a direction generally outwardly from the axis. The dispenser also includes a web which generally fills the space within to present a generally closed, centrally disposed gripping section. The web and the band have overall dimensions greater than the width of an adult thumb and finger for facilitating access to the series of O-rings and to facilitate detachment of the O-rings from the band.

In preferred embodiments, the band and the web have a circular configuration with overall dimensions no greater than twice the distance between the point of contact of the thumb and finger on the central web and adjacent regions of the user's hand adjacent the palm. In this manner, the dispenser may be rotated about the aforementioned axis in an arc of 360 degrees so that all of the O-rings around the entire length of the band may be brought in seriatim fashion toward a particular, convenient access position as the user spins the dispenser about the axis.

DESCRIPTION OF THE PREFERRED EMBODIMENT

Figure 1:
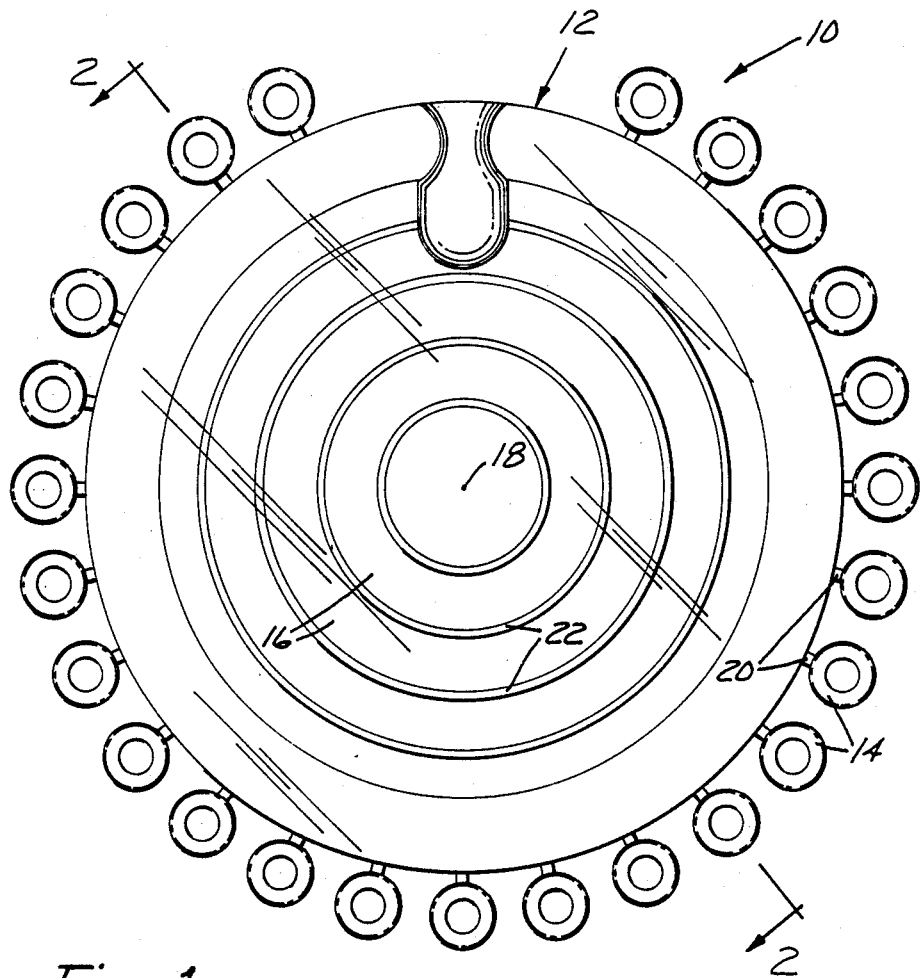
FIG. 1 is an enlarged plan view of a orthodontic O-ring dispenser constructed in accordance with a preferred embodiment of my invention.
Figure 2:
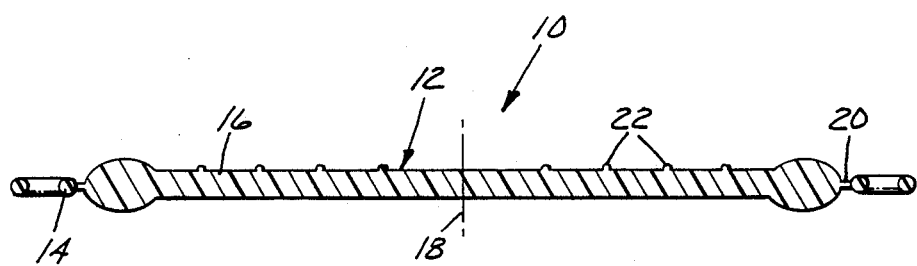
FIG. 2 is a side cross-sectional view of the dispenser taken along lines 2—2 of FIG. 1.

An orthodontic O-ring dispenser 10 is illustrated in FIGS. 1 and 2 and is molded in unitary fashion from elastomeric materials suitable for use in orthodontic treatment. Broadly speaking, the dispenser 10 includes a carrier band 12, a series of O-rings 14 and a centrally disposed web 16 which functions as a gripping section.

The carrier band 12 extends in an arc about a central reference axis 18 along a circular, closed loop path. The O-rings 14 are spaced apart from each other and are located along substantially the entire outer circumference of the carrier band 12. Each O-ring 14 is integrally connected to the carrier band 12 by a frangible section 20, and each of the sections 20 along with the O-rings 14 extends in a direction radially outwardly from the axis 18.

The O-rings 14 depicted in FIGS. 1 and 2 are adapted for use as ligatures to releasably secure an orthodontic archwire to brackets mounted on teeth. Alternatively, other types of elastomeric, ring-shaped orthodontic devices could be utilized, including tooth separators, force modules for urging brackets and their associated teeth toward desired locations, as well as other types of devices having ring-shaped portions.

The web 16 extends inwardly from the carrier band 12 toward the axis 18 and is integrally connected to the band 12 along its entire inner peripheral extent. As can be appreciated by reference to FIG. 2, the web 16 is thinner in a direction along the axis 18 than the thickness of the carrier band 12. The web 16 is also formed with a plurality of raised, concentric ribs 22 for enhancing the user's grasp of the dispenser 10. The web 16, the carrier band 12, the frangible sections 20 and each of the O-rings 14 lie in a common plane transverse to the reference axis 18.

In use, the web 16 is gripped by the practitioner between the thumb and a finger (typically the forefinger) on opposed sides of the web 16 and in respective positions generally aligned with the axis 18. The O-rings 14 that are disposed in front of the user's hand can then be conveniently detached from the carrier band 12 by grasping each O-ring with a tool and pulling the O-ring in a direction away from the axis 18 until the frangible section 20 is broken and the O-ring 14 is separated from the band 12.

Once the O-rings 14 in front of the practitioner's hand are detached from the band 12, the dispenser 10 is rotated about the axis 18 to bring remaining O-rings 14 in seriatim manner into a convenient access location in front of the hand. To this end, the user may rotate the dispenser 10 with his or her middle finger while the thumb and forefinger remain in contact with the web 16 so that a firm grip on the dispenser 10 is maintained at all times.

Advantageously, the dispenser 10 is constructed to provide substantial tactile feedback to the user so that the user can judge the position of the dispenser 10 in his or her hand without visual observation. Since the carrier band 12 is of greater thickness than the web 16, the user can sense when his or her thumb or forefinger has reached the periphery of the web 16 and touched the band 12, so that the dispenser 10 can be repositioned if necessary toward a central location wherein the axis 18 is centered about the point of contact between the thumb and forefinger. In addition, the concentric ribs 22 and the band 12 cooperatively provide resistance to sliding motion when gripped between the thumb and forefinger even though substantial forces may be utilized to tear the sections 20 when detaching the O-rings 14 from adjacent regions of the carrier band 12.

In practice, good results are observed when the dispenser 10 has an overall diameter in the range of about 3.7 cm. to about 3.9 cm., the carrier band 12 has an outer diameter in the range of about 2.9 cm. to about 3.2 cm. and the web 16 has an outer diameter adjacent the inner periphery of the band 12 in the range of about 2.2 cm. to about 2.8 cm. In such a device, the thickness of the carrier band 12 may be about 0.24 cm., greater than twice the 0.10 cm. thickness of the web 16.

One advantage of the present invention is that by utilizing the above dimensions, about 25 O-rings 14 are initially provided which represents a number sufficient for replacing all of the ligatures of a single patient. After use, the carrier band 12 along with any remaining O-rings 14 can be disposed of which reduces the likelihood of cross-contamination between patients as may occur with conventional dispensers that are provided with a much larger quantity of O-rings. Good results may also be observed when the number of O-rings 14 mounted on band 12 is in the range of about 20 to about 30. For devices other than ligatures, the number of devices carried by the dispenser 10 would be selected from a quantity suitable for use with a single patient.

I claim:

1. An orthodontic O-ring dispenser comprising:
   a carrier band extending about a reference axis along a closed loop path;
   a series of elastomeric, orthodontic O-rings integrally, detachably connected to the periphery of said carrier band, said O-rings being spaced apart from each other and extending in a direction generally outwardly from said axis; and
   a web generally filling the space within said carrier band to present a generally closed, centrally disposed gripping section, said web and said band having overall dimensions greater than the width of an adult thumb and finger for facilitating access to said series of O-rings and detachment of said O-ring from said band, said web having a thickness less than the thickness of said carrier band.

2. The dispenser of claim 1, wherein said dispenser is of a size to enable rotation of said dispenser in an arc of 360 degrees about said axis without contacting regions adjacent the user's hand when said web is gripped between said thumb and finger.

3. The dispenser of claim 1, wherein said carrier band has a generally circular configuration.

4. The dispenser of claim 1, wherein said carrier band, said web and said O-rings lie in a generally common plane.

5. The dispenser of claim 1, wherein said web is provided with a series of raised ribs.

6. The dispenser of claim 5, wherein said ribs are circular and generally concentric with said axis.

* * * * *